United States Patent
Nomoto et al.

(10) Patent No.: US 8,369,913 B2
(45) Date of Patent: Feb. 5, 2013

(54) OPTICAL MEASUREMENT INSTRUMENT FOR LIVING BODY SEMICONDUCTOR LASER INSTALLATION FOR LIVING BODY LIGHT MEASURING DEVICE

(75) Inventors: Etsuko Nomoto, Sagamihara (JP); Tsukuru Ohtoshi, Hanno (JP); Masashi Kiguchi, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 1223 days.

(21) Appl. No.: 11/984,279

(22) Filed: Nov. 15, 2007

(65) Prior Publication Data

US 2008/0234560 A1 Sep. 25, 2008

(30) Foreign Application Priority Data

Mar. 23, 2007 (JP) ................... 2007-076844

(51) Int. Cl.
*A61B 5/1455* (2006.01)
(52) U.S. Cl. .......... 600/310; 600/322; 600/323
(58) Field of Classification Search .......... 600/310, 600/322, 323, 326, 328, 316, 324, 331, 340; 372/23, 97
See application file for complete search history.

(56) References Cited

U.S. PATENT DOCUMENTS

| | | | |
|---|---|---|---|
| 5,203,329 A * | 4/1993 | Takatani et al. | 600/334 |
| 5,291,884 A * | 3/1994 | Heinemann et al. | 600/322 |
| 5,638,816 A * | 6/1997 | Kiani-Azarbayjany et al. | 600/316 |
| 5,782,237 A * | 7/1998 | Casciani et al. | 600/323 |
| 6,188,132 B1 | 2/2001 | Shih et al. | |
| 6,278,889 B1 * | 8/2001 | Robinson | 600/323 |
| 6,356,774 B1 * | 3/2002 | Bernstein et al. | 600/323 |
| 7,197,056 B2 | 3/2007 | Fujishiro et al. | |
| 7,218,657 B2 | 5/2007 | Kihara et al. | |
| 7,528,540 B2 | 5/2009 | Ikeda | |
| 7,558,307 B2 | 7/2009 | Kishimoto et al. | |
| 2002/0163952 A1 * | 11/2002 | Hwang et al. | 372/96 |

FOREIGN PATENT DOCUMENTS

| | | |
|---|---|---|
| EP | 0 679 890 A1 | 4/1995 |
| EP | 1 690 495 A1 | 7/2004 |
| JP | 02-290534 | 2/1990 |

(Continued)

OTHER PUBLICATIONS

European Search Report dated Jul. 24, 2008.

(Continued)

*Primary Examiner* — Eric Winakur
*Assistant Examiner* — Chu Chuan (JJ) Liu
(74) *Attorney, Agent, or Firm* — Stites & Harbison, PLLC; Juan Carlos A. Marquez, Esq; Stephen J. Weyer, Esq

(57) ABSTRACT

A living body measuring instrument having a sub-mount on which plural light-emitting devices oscillating at different wavelengths are mounted in proximity, one optical output monitoring device that detects the optical outputs of these light-emitting devices and a light source mounted on the same heat sink which are housed in one can-package, a light-receiving device that detects a signal from a living body, and a circuit that separates the optical output signals from the light-emitting devices, wherein at least one light-emitting device has a light-emitting layer including a $In_{1-x}Ga_xAs_yP_{1-y}$ quantum well layer and a barrier layer on a GaAs substrate, the strain $\epsilon$ satisfies $0.4\% \leq \epsilon \leq 1.4\%$, wherein y in the composition satisfies $0.10 \leq y \leq 0.45$, and the wavelength of the emitted light is from 700 nm to 760 nm.

13 Claims, 11 Drawing Sheets

FOREIGN PATENT DOCUMENTS

| | | |
|---|---|---|
| JP | 05-086304 | 4/1993 |
| JP | 08-103434 | 10/1994 |
| JP | 09-164722 | 12/1995 |
| JP | 09-307183 | 5/1996 |
| JP | 09-164722 | 6/1997 |
| JP | 11-186651 | 12/1997 |
| JP | 11-186651 | 7/1999 |
| JP | 2001-230502 | 2/2000 |
| JP | 2001-230502 | 8/2001 |
| JP | 2004-207420 | 12/2002 |
| JP | 2003-152281 | 5/2003 |
| JP | 2004-158666 | 6/2004 |
| JP | 2004-173826 | 6/2004 |
| JP | 2006-186243 | 12/2004 |
| JP | 2005-064483 | 3/2005 |
| JP | 2005-268753 | 9/2005 |
| JP | 2006-073877 | 3/2006 |
| JP | 2006-120884 | 5/2006 |
| JP | 2006-286737 | 10/2006 |

OTHER PUBLICATIONS

L. J. Mawst et al., "Short-Wavelength (0.7 μm > λ > 0.78 μm) High-Power InGaAsP-Active Diode Lasers", IEEE Journal of Selected Topics in Quantum Electronics, vol. 5, No. 3, May/Jun. 1999, pp. 785-791.

Ito, Ryoichi, et al., Semiconductor Lasers [Fundamentals and Application], Baifukan, 1989 pp. 236-237 (with English translation pp. 1-2).

Mawst, L.J., et al, Short-Wavelength (0.7 μm < λ < 0.78 μm) High-Power InGaAsP-Active Diode Lasers, IEEE Journal of Selected Topics in Quantum Electronics, vol. 5, No. 3, May/Jun. 1999, pp. 785-791.

Office Action issued by the Japanese Patent Office on Oct. 4, 2011 in the corresponding Japanese Patent Application No. 2007-076844 in Yes Japanese (3 pages) with English translation (6 pages).

Office Action from the European Patent Office in the corresponding European Application No. 07 021 792.2—2204 dated Sep. 5, 2012.

\* cited by examiner

OPTICAL MEASUREMENT INSTRUMENT FOR LIVING BODY SEMICONDUCTOR LASER INSTALLATION FOR LIVING BODY LIGHT MEASURING DEVICE

CLAIM OF PRIORITY

The present application claims priority from Japanese application JP2007-076844, filed on Mar. 23, 2007, the content of which is hereby incorporated by reference into this application.

BACKGROUND OF THE INVENTION

1. Field of the Invention

The present invention relates to an optical measurement instrument using a semiconductor light-emitting device, and in particular to a living body measuring instrument using light and a light source operating in a wavelength range from the visible to the infrared used in this device.

2. Description of the Related Arts

Spectroscopy using a light source in a wavelength range from the visible to the infrared is a widely practiced technique, and wavelengths suitable for measuring information pertaining to the living body have been indicated. For example, according to Patent Document 1 (JP-A Hei 2-290534), it is widely known that specific light wavelengths ranging from the visible to the infrared are absorbed by metabolic substrates, and the use of wavelengths of 700 nm to 1300 nm is preferred since their scattering in biological tissues is small and their absorption by water is small.

In Patent Document 1, the light source used to measure deoxy-hemoglobin concentration of blood uses two wavelengths, 760 nm which is a unique absorption wavelength of this substance, and a wavelength near this wavelength (e.g., 800 nm), or three wavelengths including these two wavelengths at which there is a large difference in the absorption coefficient of the substance and an intermediate wavelength.

To measure the concentration of oxy-hemoglobin at the same time as that of deoxy-hemoglobin, a total of four wavelengths, i.e., a unique absorption wavelength at which there is a difference between the two hemoglobins, e.g., 650 nm, a wavelength near this wavelength, an absorption wavelength at which the absorption of the two hemoglobins is the same, e.g., 805 nm, and a wavelength near this wavelength, are used. Patent Document 1 discloses that prior to performing living body light measurement, the shape of the living body must be determined by x-ray CT (computed tomography) or NMR (nuclear magnetic resonance).

Patent Document 2 (JP-A Hei 8-103434) discloses that, in an instrument that measures information in a living body using only light, an information processing method is performed wherein a light source is intensity-modulated at an arbitrary frequency, and a signal from the living body is processed by a lock-in-amplifier or the like and displayed as time series data. It is mentioned that a semiconductor laser diode may also be used as the light source, but no detailed description is given except as regards to wavelength.

When semiconductor lasers are used as plural light sources having different oscillation wavelengths for these measurements, the devices in a commercial can-package are used alongside each other. In semiconductor laser devices of the conventional art, there is usually a semiconductor laser of one wavelength in one can-package.

As an exception, Patent Document 3 (JP-A Hei 11-186651) discloses semiconductor lasers having two wavelengths, i.e., 780 nm for CD read and 650 nm for DVD read/write used in optical disk record regeneration devices installed on a submount in one can-package, which is commercially available. Further, Patent Document 4 (JP-A 2001-230502) discloses a technology wherein semiconductor lasers having three wavelengths, i.e., a wavelength of 405 nm for Blu-Ray or HD-DVD record regeneration in addition to the first two wavelengths, are simultaneously housed in one can package. These semiconductor lasers having plural wavelengths are not made to oscillate simultaneously due to their different applications.

Patent Document 5 (JP-A 2006-186243) discloses a light source wherein semiconductor lasers having three wavelengths are disposed in proximity to each other in one package. These three wavelengths correspond for example to red, green and blue for display applications. By using a can-package housing semiconductor lasers having plural wavelengths, devices that contain this light source can be made more compact.

The semiconductor lasers used as a light sources in measurement instruments, optical disk record regeneration devices and displays, must be detected an optical output, and provided with an electrical feedback circuit to stabilize the optical output. The optical output detection method may be for example a front monitor method which is frequently used in optical disk record regeneration devices (Patent Document 6 (JP-A 2004-207420)), or a rear monitor method used with semiconductor lasers for commercial products (Non-patent Document 1 (Ryoichi Ito, Michio Nakamura, Semiconductor Lasers [Fundamentals and Application], Baifukan, (1989), p.236)).

Since, in the former front monitor method, the semiconductor lasers having plural wavelengths are not often driven simultaneously, it there is usually one optical output power monitoring device, and in Patent Document 6, a device is disclosed wherein plural lasers are operated on a time-sharing basis, and an optical output power is detected in synchronism with their operation interval.

In the latter rear monitor method, as described in Patent Document 7 (JP-A Hei 9-164722), there is a printing device having a light intensity corrector that uses one optical output power monitoring device for the light from plural light-emitting points. Since these beam-emitting elements are used for printing applications, they use an identical wavelength at which the photoreceptor that detects the light has a good sensitivity, and they are not made to emit light simultaneously.

In the wavelength range of 700 nm-1300 nm which is described as preferable in Patent Document 1, since it is difficult to improve the characteristics and reliability of semiconductor lasers oscillating at a wavelength of 700 nm to 760 nm, there are very few of them on the market. The active layer material may be obtained by increasing the Al proportion of AlGaAs, by making GaInP highly strained, or by adding As to GaInP. According to Non-patent Document 2 (IEEE Journal of Selected Topics in Quantum Electronics, Vol.5, No.3, p.785-791 (1999)), when the quantum well layer is InGaAsP (strain 1.6%), a wavelength of 730 nm is obtained, but the strain is large and these lasers are not reliable. Also, in Patent Document 8 (JP-A Hei 9-307183), there is a numerical limitation of $y \leq 0.15$ in an $In_{1-x}Ga_xAs_yP_{1-y}$ quantum well layer, and the wavelength is 635 nm which is not contained within the wavelength range of the present invention.

SUMMARY OF THE INVENTION

In the conventional art, living body light measuring devices are usually used only by a few medical institutions or research organizations, and for these devices to have wider application, they need to be more compact. Likewise, a light source having plural light-emitting devices of different wavelengths which are part thereof, needs to be more compact. One solution to this problem is to use a light source having plural wavelengths mounted on one sub-mount, such as is disclosed in disc recorder regeneration device applications or display applications, and house it in one can-package.

Another problem is increasing the precision of living body light measuring devices. Since the state of a living body is constantly changing and it is difficult to distinguish the measurement signal from noise, which tends to lead to confusion, the optical output and the wavelength of the light source must be stable. Hence, since the noise in the signal from a living body is of the order of 1%, the optical output fluctuation of the light source must be less than 0.1%.

Regarding the method of detecting the optical output of these semiconductor lasers, the problem in the conventional front monitor method is that when the optical output power monitoring device used for detection is taken out of the can-package in which the semiconductor laser is housed, the number of components increases. On the other hand, in the rear monitor method, the optical output power monitoring device used for detection can be mounted on the same heat sink as the light-emitting devices, and housed in one can-package.

In Patent Document 5, a diagram is disclosed wherein optical output power monitoring devices of equal number to a number of semiconductor laser diodes are installed to the rear of the semiconductor lasers, but the detection method is not described in detail. In another method wherein plural semiconductor lasers used for living body measurement are operated simultaneously in a certain time interval, in the layout of Patent Document 5, the rear optical output of the semiconductor laser installed in front of one optical output power monitoring device and the rear optical output of the semiconductor laser adjacent to it are both input, so there is a possibility that a correct optical output power detection might not be possible, and it is difficult to separate the influence of the adjacent device.

Further, in the wavelength band from 700 nm to 1300 nm which is described as preferred in Patent Document 1, in semiconductor lasers that oscillate at a wavelength of 700 nm to 760 nm, the active layer material is AlGaAs used for 780 nm band lasers where the Al proportion is increased, GaInP used in the 600 nm band which was highly strained, or InGaAsP which is difficult to obtain by crystal growth. In the case of AlGaAs, when the Al proportion is large, oxidation occurs easily and reliability decreases, and since the difference of composition from the AlGaAs cladding layer is small, confinement of the carrier is impaired which may lead to a deterioration of characteristics. With GaInP, if the material is highly strained, crystal defects tend to occur and reliability decreases. As for InGaAsP, it is said that crystal growth of this material is difficult, and there are very few reports. Hence, since it is difficult to improve the characteristics and reliability of light-emitting devices in this wavelength band, there are very few on the market.

The problem therefore is to develop technology to improve the characteristics and reliability of semiconductor lasers in this wavelength band, and allow them to be manufactured stably.

It is therefore an object of the present invention to provide, as a light source for living body measurement, a compact light source wherein light-emitting devices oscillating at plural different wavelengths from the visible to the infrared are housed in one can-package, and an optical measurement instrument for a living body on which this light source is mounted. It is a further object of the invention to provide a design in which the characteristics of semiconductor lasers oscillating at a wavelength of 700 nm to 760 nm, which are difficult to acquire on the market as light sources for living body measurement, are stable and highly reliable.

To attain the aforesaid object, the invention provides a design wherein plural semiconductor light-emitting devices oscillating at plural different wavelengths from the visible to the infrared are mounted on one sub-mount in proximity to each other together with one optical output power monitoring device that detects the optical output of these semiconductor light-emitting devices on the same heat sink, the whole being housed in one can-package, and having a circuit which separates the optical output signals from the light-emitting devices from the detection signal of the optical output power monitoring device. The method used by the circuit may be to modulate the semiconductor light-emitting devices at plural frequencies and separate the signals by a lock-in-amplifier, to operate the semiconductor light-emitting devices on a time division basis and perform detection in synchronism with their operation, or a combination of the both methods.

FIG. 1 and FIG. 2 show the basic construction of the invention. FIG. 1 shows the construction of a light source used in the optical measurement instrument of the invention, three of the plural semiconductor lasers being shown in the diagram. Semiconductor lasers 1 to 3 are joined to a sub-mount 4 by solder. An anode side 5 to 7 of a bonding pad and a cathode side 8 are wired to drive the semiconductor lasers. In this example, the cathode side was common, but the anode side may be common. At the same time, an optical output power monitoring device 9 is disposed to the rear of the semiconductor lasers 1 to 3, and mounted together with the sub-mount 4 on a heat sink 10. The signal received from the optical output power monitoring device 9 arrives at a monitored signal separation circuit 11. Depending on the separated signals, electrical feedback signals such that the optical outputs of the semiconductor lasers 1 to 3 remain constant, are sent to light-emitting device driving power supplies 12 to 14.

To use this light source for living body measurement, a wavelength must be selected with reference to a unique absorption wavelength of the material to be measured. For example, as the wavelength of the light source used to measure deoxy-hemoglobin, referring to the absorption coefficients of deoxy- and oxy-hemoglobin shown in FIG. 3, two wavelengths, i.e., 760 nm which is the unique absorption wavelength of this substance and a wavelength near this wavelength (e.g., 800 nm) may be used, or three wavelengths, i.e. these two wavelengths for which there is a large difference in the absorption coefficient of this substance and one intermediate wavelength may be used. From FIG. 3, the first of these three wavelengths is selected from a region just below 730 nm at which the absorption coefficient of deoxy-hemoglobin is large, and above 650 nm at which the absorption of the living body is not too large so that sufficient signal strength can be obtained (e.g., 690 nm). The second is a wavelength selected from a region just above 830 nm at which the absorption coefficient of oxy-hemoglobin is large (e.g., 830 nm). The third is selected at 760 nm, which is between these two wavelengths. Since the absorption coefficient of deoxy-hemoglobin has a local maximal value between 750 nm to 760 nm, at this wavelength the absorbed signal increases, and it is a unique absorption wavelength which contributes to enhancing measurement precision. Therefore, selecting one wavelength of the light source in the range 750 nm to 760 nm is advantageous.

When selecting the first wavelength, referring to safety standards (JISC6802) and world standards (IEC60825) for laser products, if a wavelength above 700 nm is selected, the permissible strength can be increased even for the same class of laser and the measurement signal can be increased, so precision can be increased. Since there is little scattering in biological tissue, measurement precision can be increased even while respecting safety standards, so selecting a wavelength above 700 nm is advantageous.

The light generated from the light source having the construction of FIG. 1 may be guided into an optical fiber and transmitted as it is, may be propagated in the air, or a living body may be exposed to it directly. If it is guided into an optical fiber, the original optical power is attenuated in the optical fiber, so the optical output of the light source must be designed for fiber output with due regard to safety. On the other hand, in the case of air propagation and living body exposure, there are safety restrictions on the optical output of the light source depending on wavelength. From safety considerations, to ensure safety of the operator's eyes, there is a restriction on the light intensity in a circle of diameter 7 mm corresponding to the pupil size at a distance of 10 cm which is the shortest focal distance, therefore the light should be made to diverge using a light diverging modality such as a lens or the like.

From FIG. 3, it is seen also that the absorption coefficient of deoxy-hemoglobin in the region below 805 nm is sensitive to wavelength fluctuations, so wavelength fluctuations are preferably small. According to semiconductor laser catalogs, the wavelength specification is set to ±10 nm. If the optical source is disposed in proximity to the living body, considering that there may be a wavelength variation from a room temperature of 25° C. to about 50° C. which results from adding 10° C. due to the heat of the device to the body temperature of about 40° C., the wavelength fluctuation rate relative to temperature variation is 0.2 nm/K, so the wavelength fluctuation would be about 5 nm. In addition, if sufficient tolerance is allowed for compositional variations in the active layer per lot during fabrication, the wavelength fluctuation would then be double this, i.e., about ±5 nm.

In an optical measurement instrument where the subject is directly exposed to the light source, fluctuation of the light source due to optical feedback from the subject leads to measurement errors, so some tolerance must be allowed. In one solution, it is preferred to set the reflectance of the front facet high so that the reflected optical feedback from the subject does not enter the resonator of the semiconductor laser. In the case of an edge-emitter semiconductor laser, if silicon dioxide and silicon nitride which are well known materials, are alternately laminated respectively to a quarter-wave film thickness, a film having a high reflectance of about 50% is obtained. If plural growth cycle layers are stacked, a film of even higher reflectance can be manufactured and a better tolerance can be obtained. In a vertical cavity surface emitting laser, in a stacked film of semiconductor AlGaAs, a reflectance exceeding 95% is often used. A light-emitting diode may also be used as the light-emitting device, and in this case the light is not coherent from the beginning, which is robust to optical feedback.

If on the other hand it is desired to decrease the reflectance of the light source and increase the optical output from the front facet, another solution is to convert the longitudinal mode to multimode by self-pulsation so that coupling is more difficult, which is a technique known in the art.

When biological information is to be measured in proximity to a living body using this optical source, positioning is easier by using a probe, in which the optical source device brought into intimate contact with the living body, and a detector that detects light that has been partially absorbed by the living body and fed back, are disposed in an optimum position. The optical source has at least two light-emitting devices having different light emission wavelengths, and these light-emitting devices are operated either by intensity modulation of different frequencies or by time division. By having plural these optical sources and detectors, and using probes disposed in two dimensions, a wide variety of biological information can be obtained in one session.

Next, the method of implementing the semiconductor light-emitting device oscillating at a wavelength of 700 nm to 760 nm, will be described in detail.

As an active layer which can provide this wavelength region, we have selected InGaAsP on a GaAs substrate which is difficult to manufacture since a suitable crystal growth technique had not been developed. Using a metal organic vapor phase epitaxy (MOVPE) system and experimentally optimizing the growth conditions, we have succeeded in obtaining epitaxial growth of InGaAsP having a film thickness corresponding to that of the active layer of a semiconductor laser on a GaAs substrate. The growth conditions are within the normal range when using a GaAs substrate, but each system must be optimized.

FIG. 12 shows a light-emitting device oscillating at a wavelength of 700 nm to 760 nm. On an n-type GaAs substrate 201, an n-type GaAs buffer layer 202, an n-type AlGaInP cladding layer 203, an n-type AlGaInP optical guiding layer 204, a strained quantum well active layer 205, a p-type AlGaInP optical guiding layer 206, a first p-type AlGaInP cladding layer 207, a second p-type AlGaInP cladding layer 208, a p-type GaInP capping layer 209 and a p-type GaAs capping layer 210 are grown sequentially by the MOVPE method.

The second p-type AlGaInP cladding layer 208, p-type GaInP capping layer 209 and p-type GaAs capping layer 210 are formed in a striped shape by a predetermined etching, the side walls of the stripes being subjected to passivation by a dielectric film 211. Moreover, on the p-type GaAs capping layer 210, a p-side electrode 212 is formed, and under the n-type GaAs substrate 201, an n-side electrode 213 is formed.

The strained quantum well active layer 205 includes an $In_{1-x}Ga_xAs_yP_{1-y}$ ($0.10 \leq y \leq 0.45$) quantum well layer (lattice constant $a_w$ in the surface), and $(AlGa_{1-z})_wIn_{1-w}P$ barrier layer. The strain of the InGaAsP quantum well layer can be determined by experiment to evaluate characteristics and reliability. As a result of theoretical calculation and experiment, it is clear that the strain $\epsilon$ defined by $\epsilon(\%)=(a_w-a)/a \times 100$ is preferably $0.4\% \leq \epsilon \leq 1.4$. In particular, when the wavelength is from 700 nm to 720 nm, $0.4\% \leq \epsilon \leq 1.2\%$ is preferred, and $0.4\% \leq \epsilon \leq 0.9\%$ is optimum. When the wavelength is from 725 nm to 760 nm, it was clear that a strain range of $0.6\% \leq \epsilon \leq 1.4\%$ is preferred.

The GaAs substrate may be an off substrate wherein the orientation is inclined from the (100) plane to the <011> direction, and the quantum well active layer 205 may be a strain-compensated structure wherein a tensile strain is applied to the barrier layer.

Here, the difference between the invention and the conventional art will be described.

According to Patent Document 1, to obtain biological information, CT measurement is required prior to optical measurement, but according to the invention, biological information can be obtained via optical measurement alone. Patent Document 2 describes that biological information can be displayed in a time series by optical measurement, but apart from the wavelength, the light source is not described in detail. According to the present invention, the signal processing theory of Patent Document 2 is used without modification, and a construction for the light source used for the optical measurement instrument and control of optical output stabilization is proposed.

Patent Documents 3, 4, 7 describe a semiconductor light source having plural semiconductor light-emitting devices installed therein, but since the main application is optical recording and optical printing, there is no way of having the respective light-emitting points function simultaneously, whereas the present invention has semiconductor light-emitting devices emit plural different wavelengths simultaneously. The fact that one optical output power monitoring device is used is in common with Patent Document 7, but whereas Patent Document 7 describes a construction wherein a control signal is fed back and the optical output is stabilized for only one device which emits in a specific time, the present invention has plural semiconductor light-emitting devices that emit light simultaneously, and by operating these at different frequencies or by time division, the signals entering one optical output power monitoring device are separated, so the output powers of the respective semiconductor light-emitting devices can be stabilized. Hence, the design is different insofar as concerns optical output power stabilization.

In the features of this optical output stabilization method, there is also a distinction from Patent Document 5. In Patent Document 5, in a semiconductor light source wherein plural light-emitting devices of different wavelength are installed, since the main application is a display, the plural light-emitting devices are operated simultaneously, but the same number of optical output power monitoring devices is provided to measure the optical outputs of these light-emitting devices. According to the present invention, to solve the problem of stabilization, the signals entering one optical output power monitoring device are separated.

In Patent Document 6, an optical output power monitoring device is placed midway in the light path in front of the plural light-emitting devices, but since the present invention is used in applications where the light source is placed in proximity with a living body, the optical output power monitoring device cannot be placed midway in the light path, and it is therefore placed to the rear of the light-emitting points of the light-emitting devices.

The light-emitting device of Patent Document 8 uses InGaAsP for the active layer, and at a light-emitting wavelength of 635 nm, it uses a composition which can be stably obtained by crystal growth even by the conventional art, but with the same design, a composition providing a wavelength band above 700 nm as in the present invention cannot be obtained. On the other hand, Non-patent Document 2 uses the same light-emitting wavelength band as that of the invention, but the present invention differs from the conventional art in that, to supply crystals which give a light-emitting device having a light-emitting wavelength of 700 nm to 760 nm which is more reliable, a limitation is placed on the composition particularly with regard to strain.

Even if all of the conventional arts are combined, they cannot measure information in proximity with a living body. The difference of the present invention from the conventional art is that it employs a light source in proximity with a living body and a detector that detects a signal from the living body, and the timing at which the light source is activated is selected, so the optical output is stabilized and the light emission wavelength is stabilized.

Further, since a light imaging device having a light emission wavelength of 700 nm to 760 nm cannot be supplied by a reliable semiconductor light-emitting device, in the conventional art, a semiconductor light source having a different wavelength range is used for living body light measurement.

The highly reliable construction of the present invention makes it possible to use a light-emitting device having a light emission wavelength of 700 nm to 760 nm for the first time as a light source of an optical measurement instrument for a living body.

As an optical measurement instrument for a living body, compared to the case where plural can-packages containing light-emitting devices are arranged alongside each other, one can-package containing light-emitting devices having plural wavelengths is used, thus permitting compactness and light-weightness. Also, by having one optical output power monitoring device that detects the optical outputs of the light-emitting devices which is mounted to the rear of and in proximity to the plural light-emitting devices, and a circuit that separates the signals from the plural light-emitting devices, the effect of adjacent devices can be separated. And, a semiconductor laser having a wavelength of 700 nm to 760 nm which has been so far difficult to manufacture, can now be supplied as a light source of living body measurement.

DETAILED DESCRIPTION OF THE PREFERRED EMBODIMENTS

Figure 1:
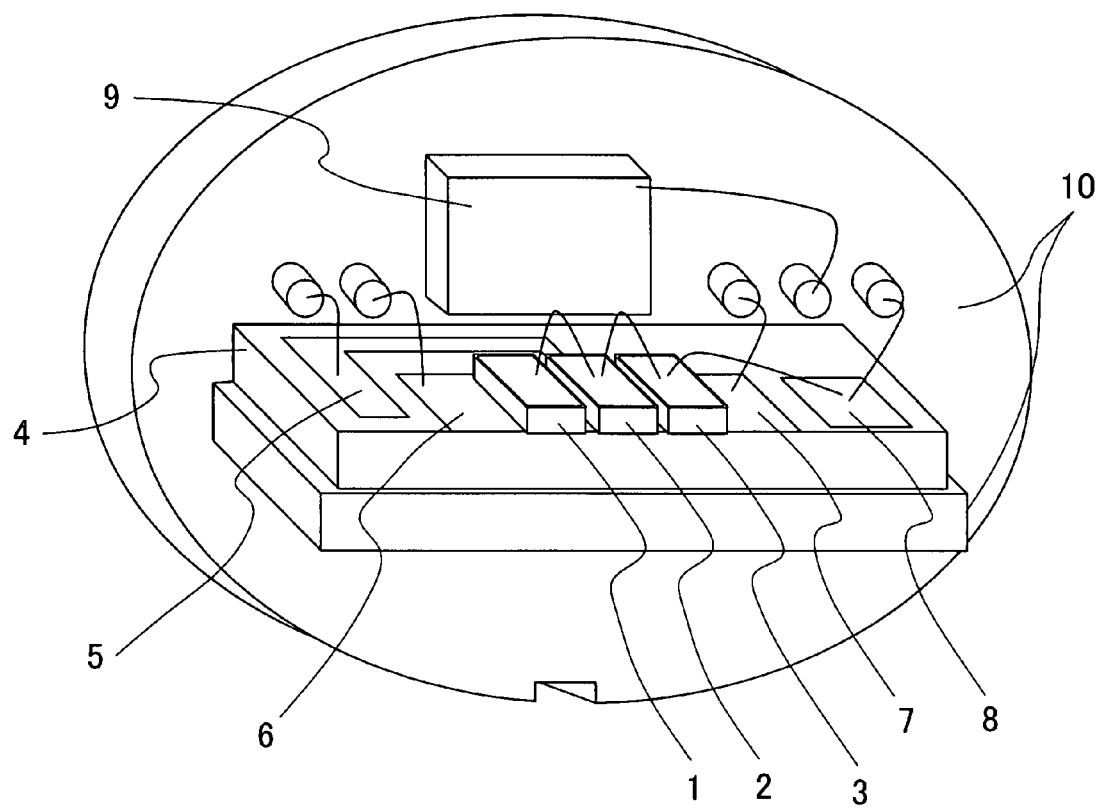
FIG. 1 is a diagram showing a semiconductor laser integrated light source according to one embodiment of the invention.

Some embodiments of the invention will now be described referring to the drawings.

First Embodiment

Figure 4:
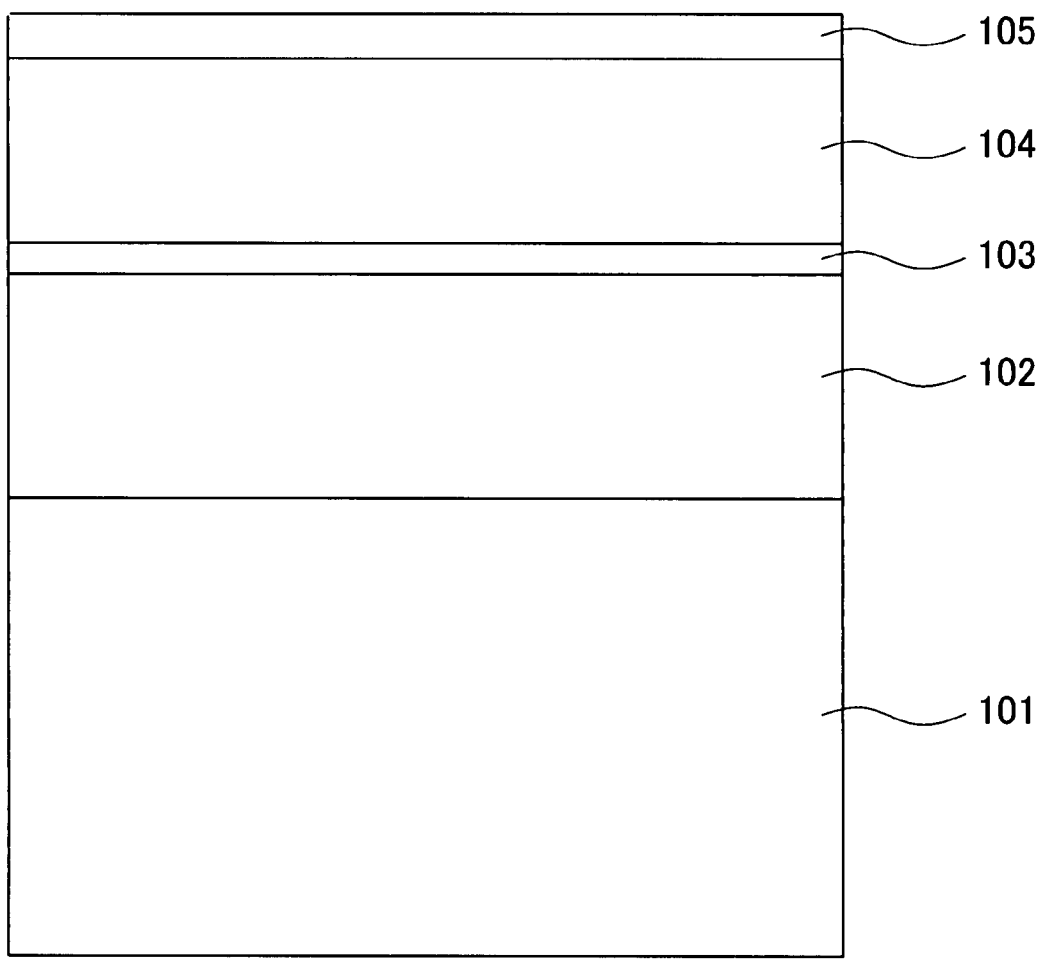
FIG. 4 is a diagram showing a semiconductor laser crystal growth structure used in the invention.

A first embodiment of the invention will be described referring to the device shown in FIG. 1 and FIG. 2. For the semiconductor lasers 1 to 3, crystals are grown in the order of an n-type cladding layer 102, an active layer 103, a p-type cladding layer 104, and a p-type contact layer 105 on an n-type GaAs substrate 101 as shown by the cross-sectional structure of FIG. 4 using a metal oxide vapor phase epitaxy (MOVPE) system. Among the three semiconductor lasers, 1, 2 targeting an oscillation wavelength below 760 nm use an AlGaInP layer of thickness 1.5 μm for the n-type and p-type cladding layers 102, 104, and a multi quantum well structure including a well layer of GaIn(As)P of thickness 10 nm and a barrier layer of AlGaInP of thickness 15 nm, together with an optical guiding layer which is an AlGaInP layer of thickness 25 nm sandwiching the structure, as the active layer 103, and use a GaAs layer for the p-type contact layer 105. The remaining semiconductor laser 3 targeting an oscillation wavelength of 800 nm uses an AlGaAs layer of thickness 1.5 μm for the n-type, p-type cladding layers 102, 104, and has a multi quantum well structure including a well layer of GaAs of thickness 10 nm and a barrier layer of AlGaAs of thickness 15 nm, together with a an optical guiding layer which is an AlGaAs layer of thickness 25 nm sandwiching the structure, as the active layer 103, and uses a GaAs layer for the p-type contact layer 105.

After forming a striped pattern by photolithography, etching is performed by a dry-etching apparatus leaving the stripes so as to form a mesa shape. In the case of the semiconductor laser 3 only, a block layer is grown including n-type doped AlGaAs and n-type doped GaAs in the part outside the stripes by selective area growth using the MOVPE system with the mask used for stripe patterning, and after removing the mask, a p-type doped GaAs contact layer is grown to bury the mesa.

Passivation is performed by silicon dioxide of thickness 350 nm at locations outside the stripes, and titanium, platinum and gold which will form the p side electrode are electron beam evaporated in sequence. After lapping the GaAs substrate to 100 μm, gold-germanium, nickel, titanium, platinum and gold which will form the n side electrode are electron beam evaporated in sequence on the back, and alloyed. Each wafer is cleaved so that the cavity length of the semiconductor laser is 800 μm. On the cleaved facet, alumina is deposited on the front surface by a sputtering device to give a reflectance of about 13%, and a stacked layer of alumina and titanium oxide is deposited on the back surface to give a reflectance of 90% or more.

The semiconductor lasers 1 to 3 fabricated in this manner are then mounted on the sub-mount 4 by junction-down. On the heat sink 10, a monitoring photodiode (hereafter, monitor-PD) 9 is first fixed by solder as an optical output power monitoring device for stabilizing the optical output of the semiconductor laser, and the sub-mount 4 on which the semiconductor lasers 1 to 3 are mounted is then fixed by solder. The wires from the semiconductor lasers 1 to 3 are connected to input/output pin via bonding pads 5 to 8. In FIG. 1, the case of a cathode common connection was shown, but it may also be anode common, which can be controlled in an identical way. The can-package is then completed by sealing with a cap (not shown). The output from the monitor PD 9 is guided to a monitored signal separation circuit 11, the separated signals are fed back to the driver power supplies 12 to 14 of the semiconductor lasers 1 to 3, and a correction is applied to eliminate optical output fluctuations.

Here, to increase the precision of spectroscopic analysis in light measurement, the semiconductor lasers 1 to 3 are modulated at frequencies which are very close to each other but different, and the monitored signal separation circuit 11 in this case may be a lock-in-amplifier.

The oscillation wavelengths of the semiconductor lasers 1 to 3 fabricated in this embodiment are respectively 690 nm, 760 nm and 830 nm. They operate at an optical output of 50 mW from 25° C. to 50° C., and the fluctuation of oscillation wavelength within this temperature range was within ±5 nm. Also, in a life test at a fixed optical power at 50° C., 50 mW, operation in excess of 2000 hours has been verified. Further, by modulating the semiconductor lasers at different frequencies, the signal monitored optical outputs detected at the rear can be separated using the lock-in-amplifier, and by performing an electrical feedback to the semiconductor laser driver power supplies 12 to 14, the fluctuation amount of the optical output was suppressed to equal to or less than 0.1%.

Second Embodiment

A second embodiment of the invention will now be described in the case of the optical measurement instrument for a living body shown in FIG. 5. An optical source 15 on which semiconductor lasers having plural wavelengths are mounted, is obtained by an identical fabrication method to that of the first embodiment. A pulse signal from a pulse generator 19 in a transmitter 18, which is controlled by a control and display personal computer 17, is supplied to a light source driver 16 as a modulated signal from a CDMA (code division multiple access) encode circuit 20 to drive the light source 15. The signal monitored optical outputs received at the rear of the semiconductor laser are separated by CDMA-decoding. This light source 15 oscillates at oscillation wavelengths of 695 nm, 780 nm and 850 nm, and at an optical output of 50 mW from 25° C. to 60° C., it operates with an optical output fluctuation of less than 0.1%. The light of three wavelengths emitted from this light source 15 has an emitting point distance of 220 μm, and this light is guided into a bundle fiber 21 having a core of diameter 1 mm. This fiber output light is frequency-modulated, a living body 22 is exposed to it, and the light fed back after absorption in the biological material is captured by a light-receiving device module 23. This light source 15 and light-receiving device module 23 are detachably fixed to a probe 24 at the optimum interval for signal processing, so positioning on the surface of the living body 22 is easy, and the module can be replaced in the event of a fault. Signal processing is performed using a receiver 27 combining an analog amplifier 25 and CDMA decode circuit 26, and analyzed/displayed by the control and display personal computer 17. The optical output fluctuation of the light source 15 is small, so the reliability of the signal is increased.

Third Embodiment

Figure 3:
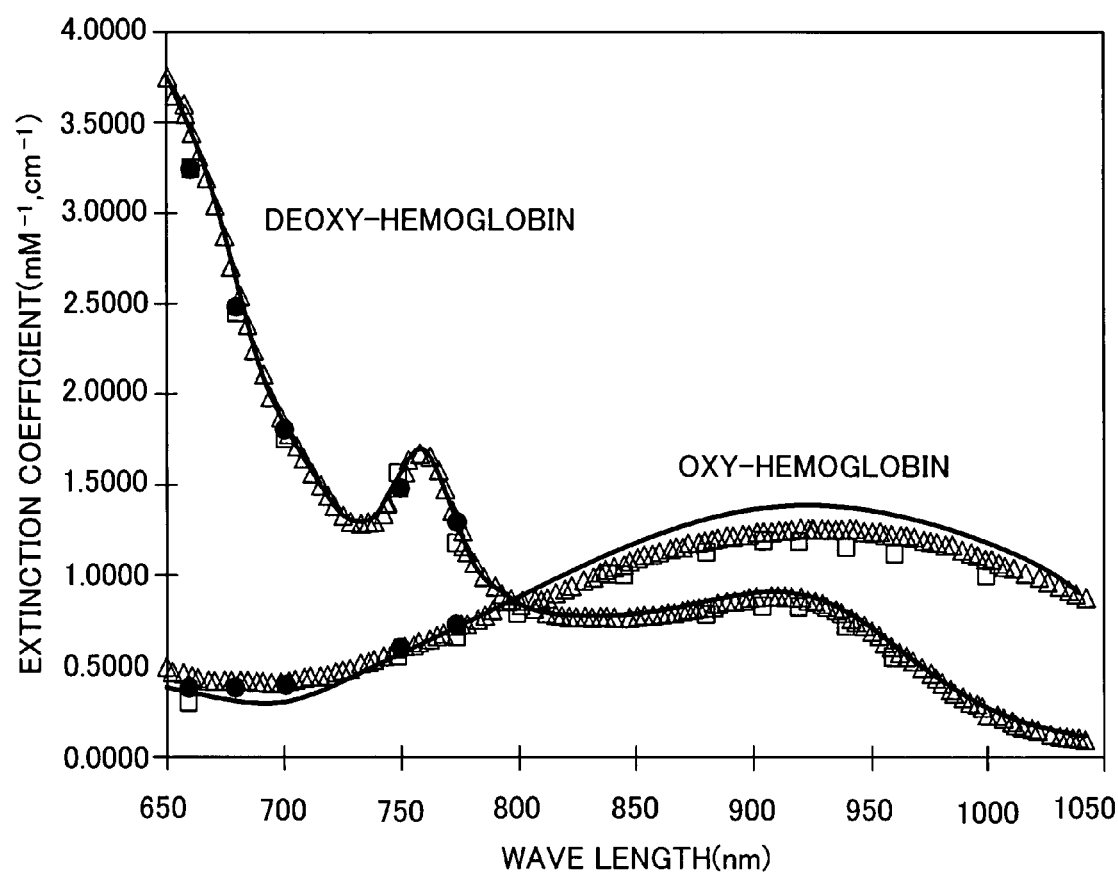
FIG. 3 is a diagram showing a wavelength dependence of an extinction coefficient of deoxy-hemoglobin and hemoglobin.
Figure 5:
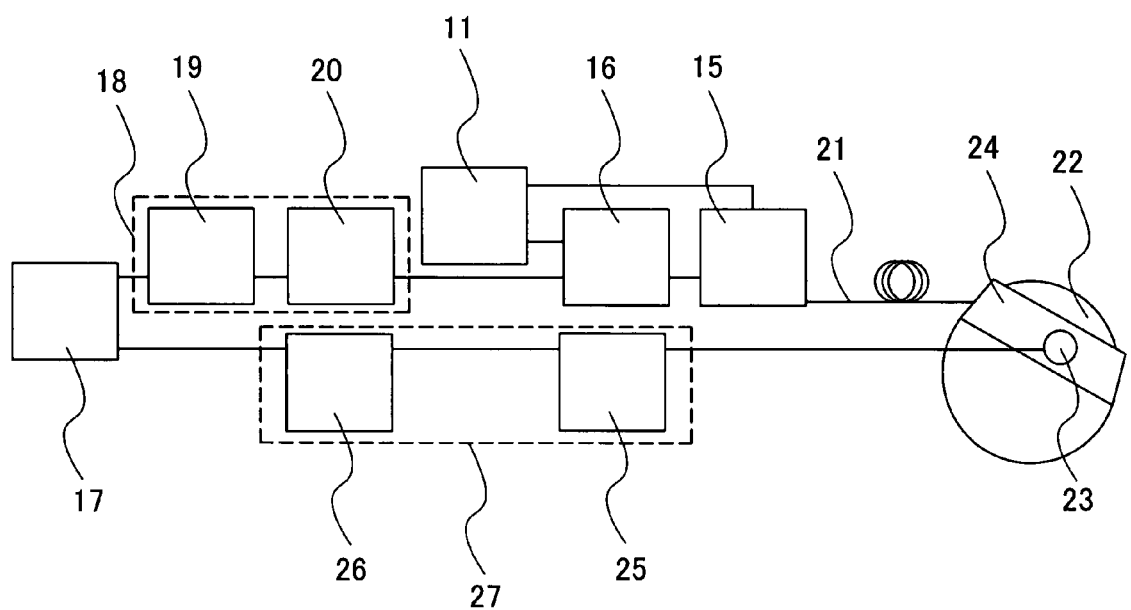
FIG. 5 is a diagram showing a living body measuring instrument using a semiconductor laser integrated light source according to one embodiment of the invention.

A third embodiment of the invention has an identical construction to the device shown in FIG. 5. The light source 15 on which semiconductor lasers having plural wavelengths are mounted is fabricated by an identical method to that of the first embodiment, oscillates at oscillation wavelengths of 680 nm, 755 nm and 830 nm, and at an optical output of 50 mW from 25° C. to 60° C., it operates with an optical output fluctuation of less than 0.1%. These wavelengths, from FIG. 3, are selected to be 680 nm at which the absorption coefficient of deoxy-hemoglobin is very high, 830 nm at which the absorption coefficient of oxy-hemoglobin is relatively high, and 750 nm, which is an intermediate wavelength. The light of three wavelengths emitted by this light source 15 is guided into the bundle fiber 21 having a core of diameter 1 mm. This fiber output light is frequency-modulated and the living body 22 is exposed to it. The light fed back after absorption in the biological material is captured by the light-receiving device module 23, signal processing is performed using the receiver 27 similarly to the second embodiment, and the signal from the living body is analyzed. The optical output fluctuation of the light source 15 is small, and since two wavelengths are selected at which there is a large difference in the absorption coefficients of deoxy-hemoglobin and oxy-hemoglobin in the measurement target, and an intermediate wavelength, a high precision measurement can be performed.

Fourth Embodiment

Figure 2:
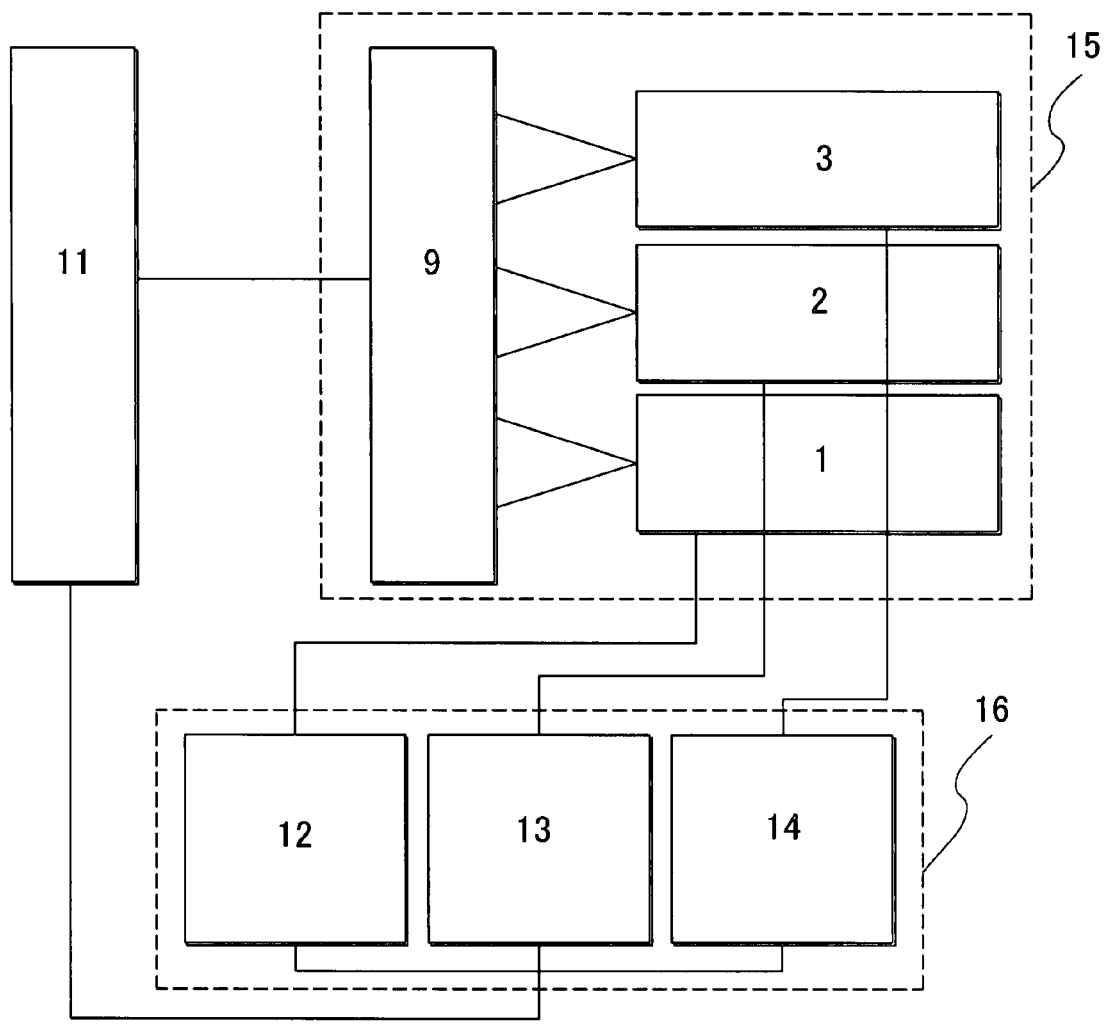
FIG. 2 is a diagram showing a semiconductor laser integrated light source and its optical output control system according to one embodiment of the invention.

In a fourth embodiment of the invention, the wavelength of the semiconductor laser of the light source device shown in FIG. 1 is limited. The active layer composition is determined so that the oscillation wavelengths of the semiconductor lasers 1, 2, 3 are respectively 705±5 nm, 755±5 nm, and 830±5 nm. The semiconductor lasers 1, 2 may be manufactured using a multi quantum well structure having an InGaAsP well layer in the active layer, and the semiconductor laser 3 may be manufactured using a multi-quantum well structure having a GaAs well layer in the active layer.

In particular, since the wavelength of 700 nm to 1300 nm is selected, which has a small scattering in biomedical tissue and a low absorption in water, a signal from the living body can be extracted with high precision. Among these, the semiconductor laser 1 has the shortest wavelength of 705±5 nm, and it is a wavelength with a small scattering in biomedical tissue at which the absorption coefficient of deoxy-hemoglobin is as high as it can be above 700 nm, considering safety standards. Also, since the semiconductor laser 2 oscillates at 750 to 760 nm which is a unique absorption wavelength having an extremely high value of absorption coefficient for deoxy-hemoglobin, the absorbed signal is large. Due to these facts, the selection of 705±5 nm and 755±5 nm as the oscillation wavelengths of the semiconductor lasers contributes to increasing measurement precision.

Fifth Embodiment

Figure 6:
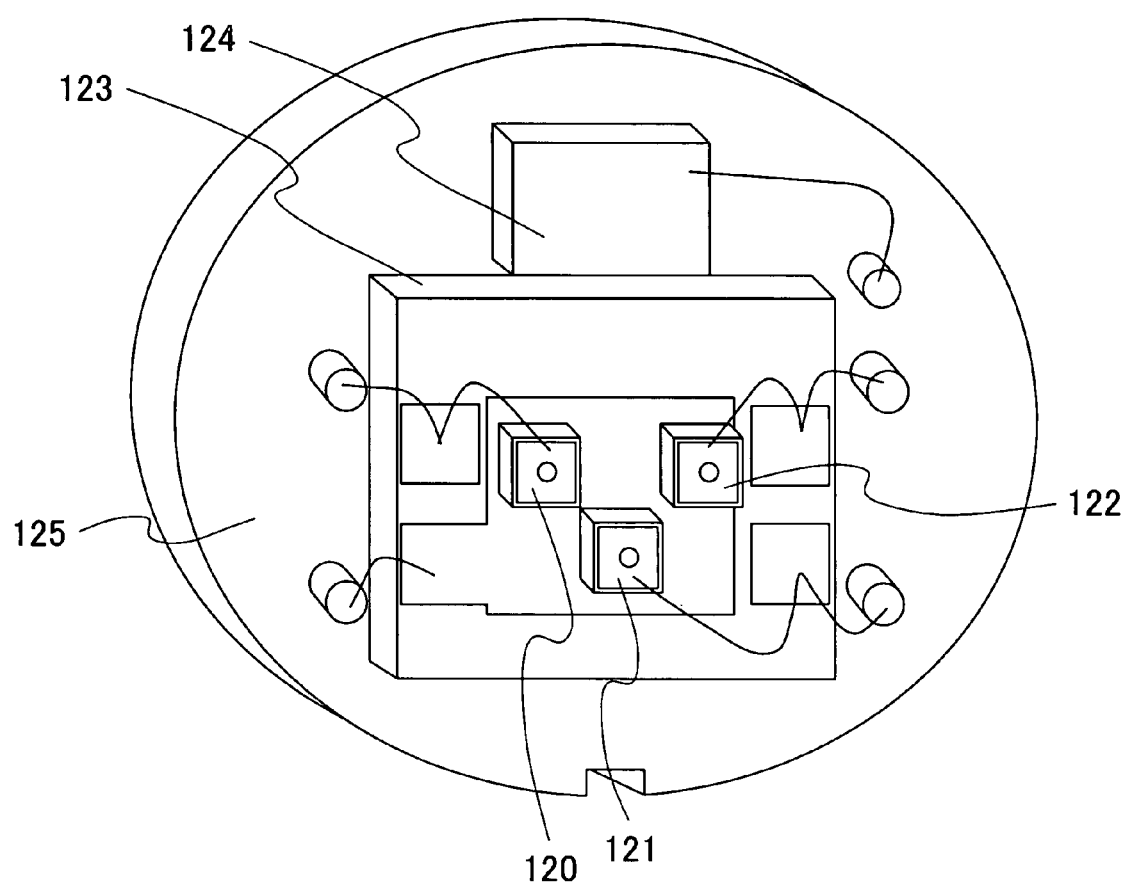
FIG. 6 is a diagram showing a semiconductor laser integrated light source according to one embodiment of the invention.
Figure 7:
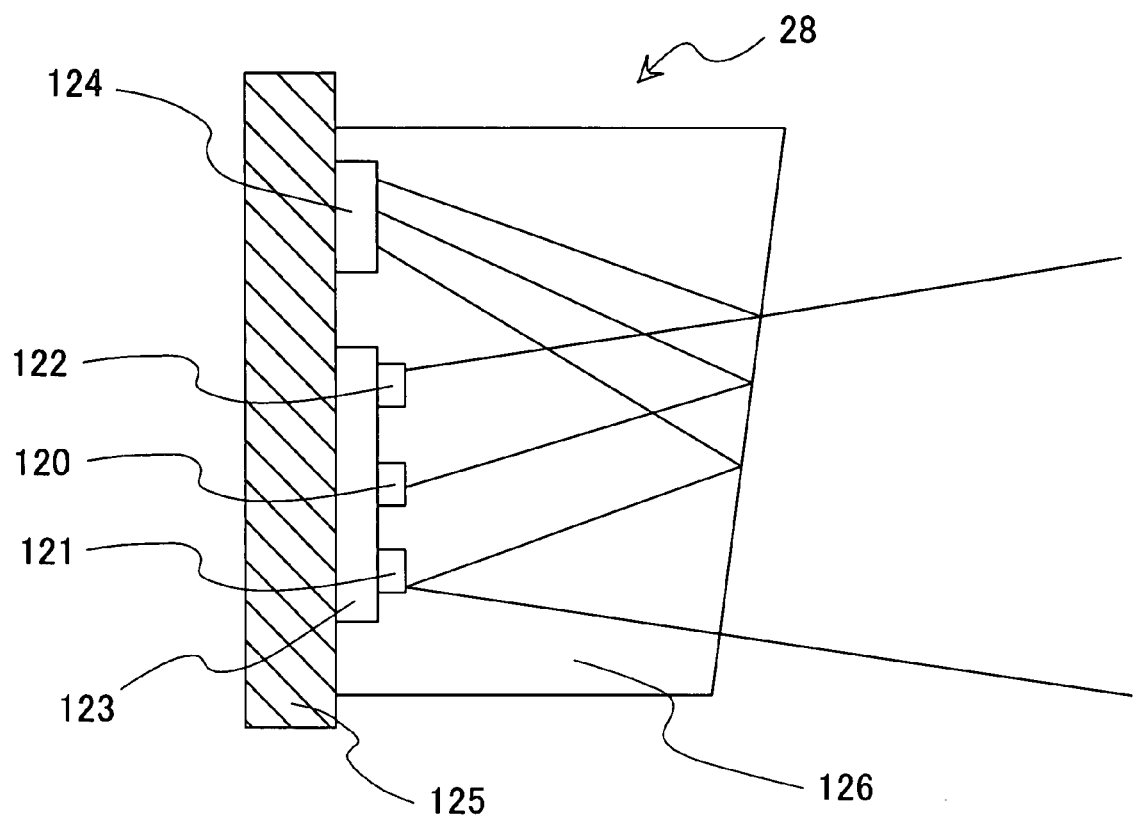
FIG. 7 is a cross-sectional view showing a semiconductor laser integrated light source according to one embodiment of the invention.

A fifth embodiment of the invention will now be described referring to the devices shown in FIG. 6 and FIG. 7. FIG. 6 is a view of the light source from the emitting facet, and FIG. 7 is a cross-sectional view from the side. The semiconductor lasers 120, 121, 122 are vertical cavity surface emitting lasers, and their wavelengths are 780 nm, 805 nm, 830 nm. These semiconductor lasers are mounted on a sub-mount 123, and fixed to a heat sink 125 together with a monitor PD 124. They are then sealed with a cap 126 which has a reflectance of about 10% at these wavelengths, having a window, which is slightly inclined from the vertical with respect to the light propagation direction. This light source 28 gave an optical output of 2 mW at each of these three wavelengths.

A construction which stabilizes the optical output will now be described referring to FIG. 8. The output from the monitor PD 124 is guided to the monitored signal separation circuit 11, the signals separated here are fed back to the light source driver 16 of the semiconductor lasers 120 to 122, and a correction is applied to eliminate optical output fluctuation. Here, to increase the precision of the spectrophotometric analysis of the living body measurement, the semiconductor lasers 120 to 122 are driven by time division, and in the monitor signal, only the signal synchronized with the semiconductor lasers 120 to 122 is detected by the monitored signal separation circuit 11. The overall construction forms a light source module 29.

The light source of this embodiment is used in proximity to the living body at a distance of several mm, and since the operating temperature is maintained at about 40° C., the wavelength fluctuation is small, and within ±5 nm for each device. Further, with a vertical cavity surface emitting laser, since the reflectance of the light-emitting surface is approximately 95%, there is optical feedback tolerance, and the optical output fluctuation is within 0.05%. Due to this, a stable signal with little noise is obtained from the living body.

The semiconductor lasers 120, 121, 122 may be replaced by light-emitting diodes. Since light-emitting diodes do not give coherent light, they have a good optical feedback tolerance.

Sixth Embodiment

Figure 9:
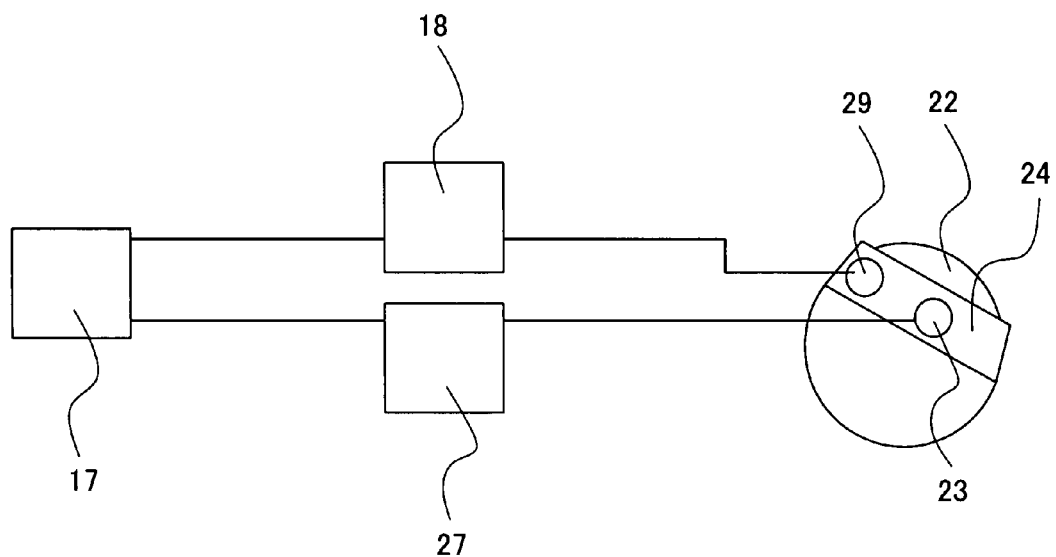
FIG. 9 is a diagram showing a living body measuring instrument using a light source module according to one embodiment of the invention.

A sixth embodiment of the invention will now be described referring to the device shown in FIG. 9. The light source module 29 on which semiconductor lasers having plural wavelengths are mounted, is obtained by an identical fabrication method to that of the fifth embodiment. Here, the lasers oscillate at two oscillation wavelengths, i.e., 780 nm and 830 nm, and in the operating temperature range of 25° C. to 40° C., at an optical output of 2 mW, the wavelength fluctuation was within ±5 nm and the optical output fluctuation was within 0.05%. This light source module 29 receives a signal that determines the operation timing by the transmitter 18, and the living body 22 is exposed to the light. The light fed back after absorption by the biomedical tissue is captured by the light-receiving device module 23. The signal is processed by the receiver 27, and analyzed/displayed by the control and display personal computer 17 as a signal from the living body.

Figure 10:
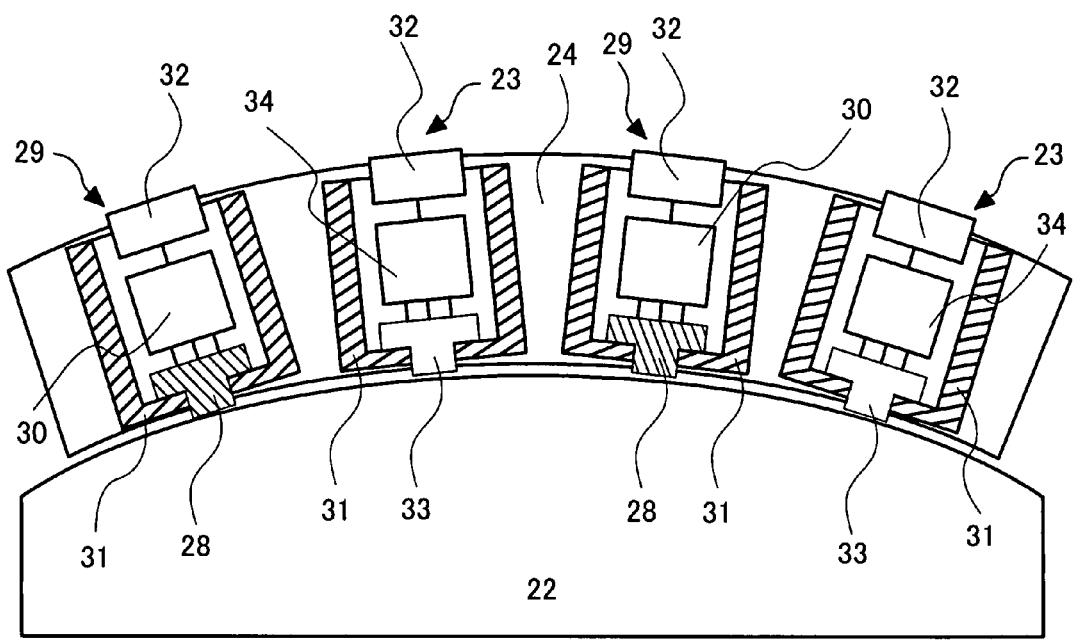
FIG. 10 is a block cross-sectional view showing a living body measuring instrument using a light source module according to one embodiment of the invention.

This light source module 29 and light receiving device module 23 are detachably fixed to the probe 24 at the optimum interval for signal processing, positioning on the surface of the living body 22 is easy, and the module can be replaced in the event of a fault. FIG. 10 shows a partial cross-section of the probe 24. The light source module 29 is housed in a case 31 together with the light source 28 and optical output stabilization circuit 30, and receives a power supply from outside by a power feeding connector 32. The light receiving device module 23 is housed in the case 31, together with an avalanche photodiode 33 and an amplifier, and a control circuit 34 containing a high voltage power supply unit, and receives a power supply from outside by the power feeding connector 32. The case 31 can be detached from the probe 24. In the diagram, two each of the light source modules 29 and light receiving device modules 23 are fixed, but more modules can be disposed in an array to obtain signals from a wider area of the living body.

Since the light source module 29 guides light to the living body, an optical fiber is not required, and the device can be made compact and lightweight, therefore, a living body light measuring device can be made compact while maintaining the measurement precision of the conventional art.

Seventh Embodiment

Figure 11:
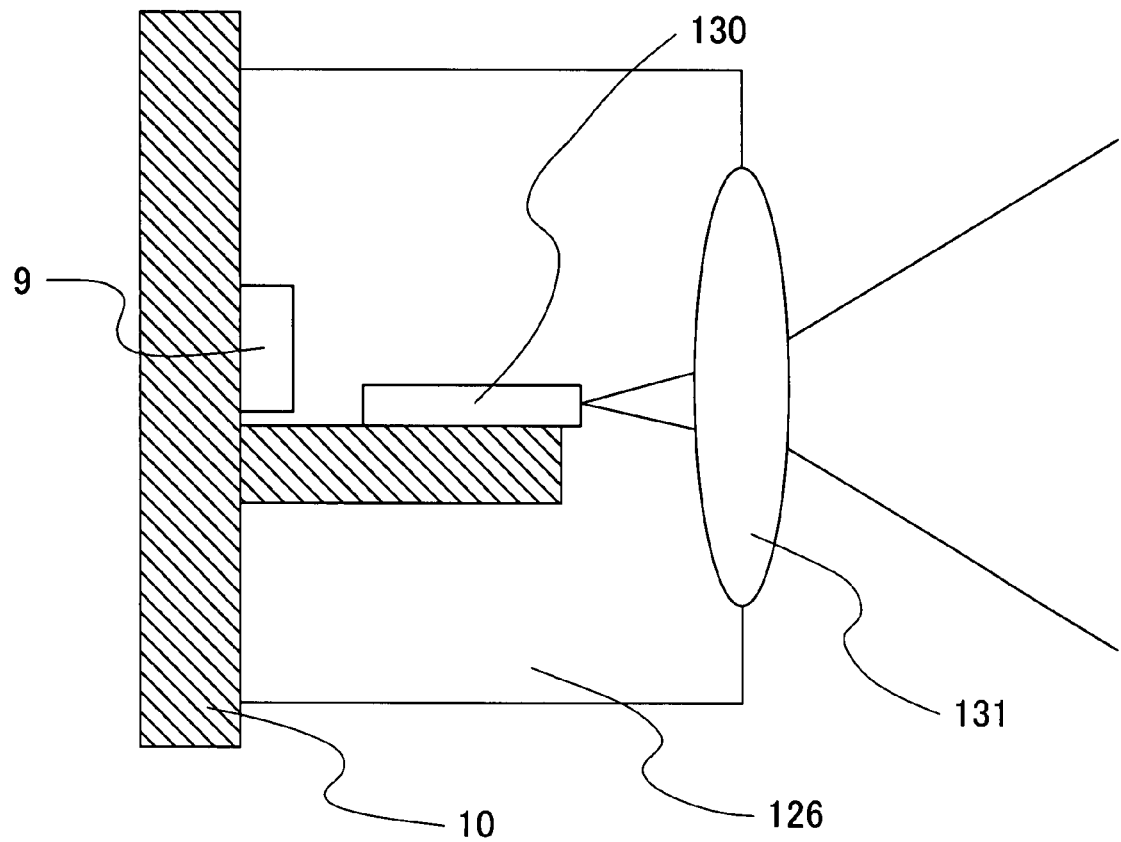
FIG. 11 is a cross-sectional view showing a semiconductor laser integrated light source according to one embodiment of the invention.

A seventh embodiment of the invention will now be described referring to the device shown in FIG. 11. A semiconductor laser 130 is an edge emitting laser fabricated by the dual wavelength integrated semiconductor laser technique known in the art, its oscillation wavelengths being 690 nm and 760 nm. The reflectance of the light-emitting surface is made 68% by forming two growth cycle layers of a quarter wave film thickness of silicon dioxide and silicon nitride. The optical output is 4 mW at these respective wavelengths. To avoid safety problems, considering the risk of the laser directly entering the observer's eyes, the optical source package has a modality that widens the beam, e.g., a lens 131.

Figure 8:
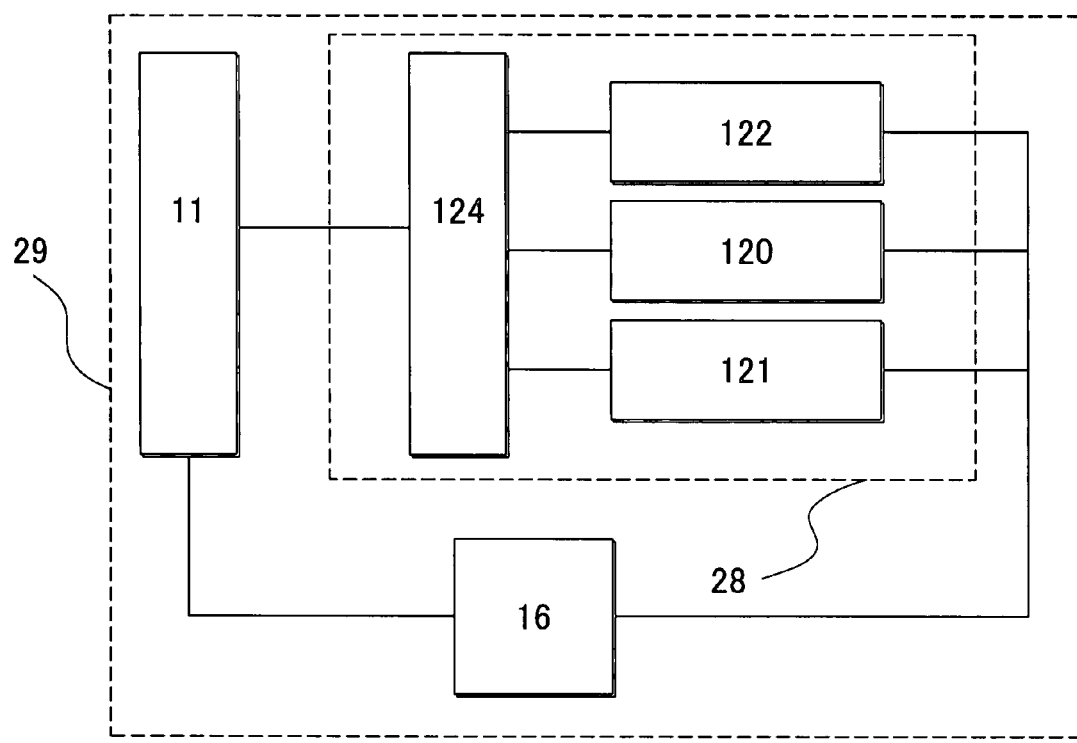
FIG. 8 is a diagram showing a semiconductor laser integrated light source and its optical output control system according to one embodiment of the invention.

The construction that stabilizes the optical output is identical to that of FIG. 8. The semiconductor laser 130 is driven by time division, and regarding the monitor signal, only a signal synchronized with light of each wavelength from the semiconductor laser 130 is detected by an identical circuit to the monitored signal separation circuit 11. Here, to improve the measurement precision, operating at plural wavelengths simultaneously is preferred since plural signals can be obtained at the same time, but a method can also be used where light of each wavelength from the semiconductor laser 130 is intensity-modulated at different frequencies, and the light intensity of each wavelength is stabilized using a lock-in-amplifier as the circuit 11 which separates the monitored signals. To improve precision still further, the light of plural wavelengths can be driven at two drive timings combined together, i.e., time division and intensity modulation at different frequencies. In both cases, a circuit identical to the monitored signal separation circuit 11 may be manufactured to separate the signals entering the monitor PD 9 according to the drive timing of the light-emitting devices.

The light source of this embodiment is used in proximity to the living body at a distance of several millimeters, and since the operating temperature is maintained at 40° C., the wavelength fluctuation was small and the fluctuation was within ±5 nm for each device. Since the reflectance of the light-emitting surface is 68%, there is optical feedback tolerance, and the optical output fluctuation is within 0.08%. Due to this, a stable signal with little noise is obtained from the living body.

Eighth Embodiment

An eighth embodiment of the invention will now be described referring to FIG. 11. Here, the semiconductor laser 130 has increased optical feedback tolerance by generating a pulsation by providing a saturable absorbing area near the facet that emits light. To stabilize the optical output, for example, in the same way as in the construction of FIG. 2, the semiconductor lasers may be driven at different frequencies, and the signals from the monitor PD may be separated by a lock-in-amplifier.

The optical source in this embodiment is used in proximity to the living body at a distance of several mm, and since the operating temperature is maintained at approximately 40° C., the wavelength fluctuation is small, and the fluctuation was within ±5 nm for each light-emitting device. Due to pulsation, the optical feedback does not couple easily, and the optical output fluctuation was within 0.08%. Hence, a stable signal with little noise can be obtained from the living body.

Ninth Embodiment

Figure 12:
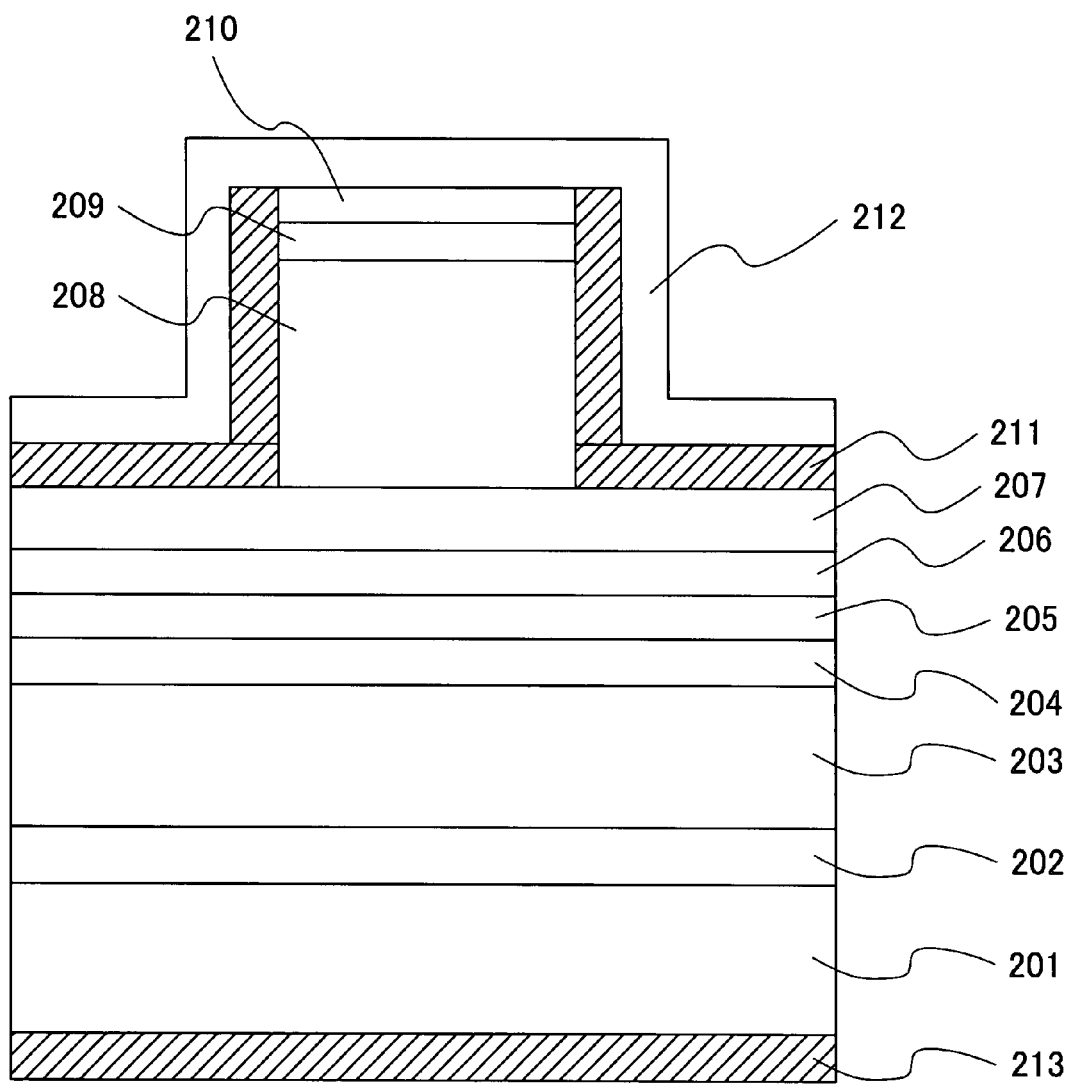
FIG. 12 is a cross-sectional view of a semiconductor laser according to one embodiment of the invention.

A ninth embodiment will be described using a cross-sectional structural view (FIG. 12) of the semiconductor laser. On a predetermined n-type GaAs substrate 201, an n-type GaAs buffer layer 202, an n-type AlGaInP cladding layer 203, an n-type AlGaInP optical guiding layer 204, a strained quantum well active layer 205, a p-type AlGaInP optical guiding layer 206, a first p-type AlGaInP cladding layer 207, a second p-type AlGaInP cladding layer 208, a p-type GaInP capping layer 209 and a p-type GaAs capping layer 210 are grown sequentially by the MOVPE method. The second p-type AlGaInP cladding layer 208, p-type GaInP capping layer 209 and p-type GaAs capping layer 210 are formed in a striped shape by a predetermined etching, the side walls of the stripes being subjected to passivation by a dielectric film 211. On the p-type GaAs capping layer 210, a p-side electrode 212 is formed, and on the n-type GaAs substrate 201, an n-side electrode 213 is formed.

According to the ninth embodiment, the strained quantum well layer 205 has an $In_{0.5}Ga_{0.5}As_{0.16}P_{0.84}$ quantum well (compressive strain 0.7%), and a $(Al_{0.5}Ga_{0.5})_{0.5}In_{0.5}P$ barrier layer. In this case, a semiconductor laser device oscillating at a wavelength of 705 nm is obtained by adjusting the quantum well thickness to within 7 to 12 nm.

By applying this to the semiconductor laser 1 of the first embodiment, a light source suitable for living body measurement can be supplied.

Tenth Embodiment

A tenth embodiment will be described using the cross-sectional structural view (FIG. 12) of the semiconductor laser. According to this embodiment, the strained quantum well layer 205 has an $In_{0.5}Ga_{0.5}As_{0.32}P_{0.68}$ quantum well (compressive strain 1.2%), and an $(Al_{0.5}Ga_{0.5})_{0.5}In_{0.5}P$ barrier layer. In this case, a semiconductor laser device oscillating at a wavelength of 755 nm is obtained by adjusting the quantum well thickness to within 7 to 12 nm.

By applying this to the semiconductor laser 2 of the first embodiment, a light source suitable for living body measurement can be supplied.

The GaAs substrate 201 may be an off substrate wherein the surface orientation is inclined from the (100) plane to the <011> direction. The strained quantum well layer 205, may be a strain compensated structure in which a tensile strength is applied to the barrier layer. The strain of the InGaAsP quantum well layer can be determined experimentally to evaluate characteristics and reliability. As a result of theoretical calculation and experiment, it has been found that $0.4\% \leq \epsilon \leq 1.4\%$ is preferred regardless of wavelength. Particularly, in the case where the wavelength is from 700 nm to 720 nm, $0.4\% \leq \epsilon \leq 1.2\%$ is preferred, and the optimum range is $0.4\% \leq \epsilon \leq 0.9\%$. Also, in the case where the wavelength is from 725 nm to 760 nm, it has been found that a strain in the range of $0.6\% \leq \epsilon \leq 1.4\%$ is preferred.

The semiconductor laser devices which can be manufactured by this embodiment and its modifications are as follows.

1. A semiconductor laser device having a light-emitting layer including an $In_{1-x}Ga_xAs_yP_{1-y}$ quantum well layer having a lattice constant $a_w$ in the surface and barrier layer provided on a GaAs substrate having a lattice constant a, wherein the strain $\epsilon$ defined by $\epsilon(\%)=(a_w-a)/a \times 100$ satisfies $0.4\% \leq \epsilon \leq 1.4\%$, wherein y in the composition satisfies $0.1\% \leq y \leq 0.45$, and the wavelength of the emitted light is from 700 nm to 760 nm.

2. A semiconductor laser device having a light-emitting layer including an $In_{1-x}Ga_xAs_yP_{1-y}$ quantum well layer having a lattice constant $a_w$ in the surface and barrier layer provided on a GaAs substrate having a lattice constant a, wherein the strain $\epsilon$ defined by $\epsilon(\%)=(a_w-a)/a \times 100$ satisfies $0.4\% \leq \epsilon \leq 1.2\%$, wherein y in the composition satisfies $0.10 \leq y \leq 0.25$, and the wavelength of the emitted light is from 700 nm to 730 nm.

3. A semiconductor laser device having a light-emitting layer including an $In_{1-x}Ga_xAs_yP_{1-y}$ quantum well layer having a lattice constant $a_w$ in the surface and barrier layer provided on a GaAs substrate having a lattice constant a, wherein the strain $\epsilon$ defined by $\epsilon(\%)=(a_w-a)/a \times 100$ satisfies $0.4\% \leq \epsilon \leq 0.9\%$, wherein y in the composition satisfies $0.10 \leq y \leq 0.20$, and the wavelength of the emitted light is from 700 nm to 720 nm.

4. A semiconductor laser device having a light-emitting layer including an $In_{1-x}Ga_xAs_yP_{1-y}$ quantum well layer having a lattice constant $a_w$ in the surface and barrier layer provided on a GaAs substrate having a lattice constant a, wherein the strain $\epsilon$ defined by $\epsilon(\%)=(a_w-a)/a \times 100$ satisfies $0.4\% \leq \epsilon \leq 1.4\%$, wherein y in the composition satisfies $0.20 \leq y \leq 0.35$, and the wavelength of the emitted light is from 700 nm to 760 nm.

5. A semiconductor laser device having a light-emitting layer including an $In_{1-x}Ga_xAs_yP_{1-y}$ quantum well layer having a lattice constant $a_w$ in the surface and barrier layer provided on a GaAs substrate having a lattice constant a, wherein the strain $\epsilon$ defined by $\epsilon(\%)=(a_w-a)/a \times 100$ satisfies $0.1\% \leq \epsilon \leq 0.45\%$, wherein y in the composition satisfies $0.4 \leq y \leq 1$, and the wavelength of the emitted light is from 700 nm to 760 nm.

6. A semiconductor laser device having a light-emitting layer including an $In_{1-x}Ga_xAs_yP_{1-y}$ quantum well layer having a lattice constant $a_w$ in the surface and barrier layer provided on a predetermined GaAs substrate having a lattice constant a, wherein the strain $\epsilon$ defined by $\epsilon(\%)=(a_w-a)/a \times 100$ satisfies $0.4\% \leq \epsilon \leq 1.2\%$, wherein y in the composition satisfies $0.10 \leq y \leq 0.25$, and the wavelength of the emitted light is from 700 nm to 730 nm.

7. A semiconductor laser device having a light-emitting layer including an $In_{1-x}Ga_xAs_yP_{1-y}$ quantum well layer having a lattice constant $a_w$ in the surface and barrier layer provided on a predetermined GaAs substrate having a lattice constant a, wherein the strain $\epsilon$ defined by $\epsilon(\%)=(a_w-a)/a\times100$ satisfies $0.4\%\leq\epsilon\leq0.9\%$, wherein y in the composition satisfies $0.10\leq y\leq0.20$, and the wavelength of the emitted light is from 700 nm to 720 nm.

8. A semiconductor laser device having a light-emitting layer including an $In_{1-x}Ga_xAs_yP_{1-y}$ quantum well layer having a lattice constant $a_w$ in the surface and barrier layer provided on a predetermined GaAs substrate having a lattice constant a, wherein the strain $\epsilon$ defined by $\epsilon(\%)=(a_w-a)/a\times100$ satisfies $0.6\%\leq\epsilon\leq1.4\%$, wherein y in the composition satisfies $0.20\leq y\leq0.35$, and the wavelength of the emitted light is from 725 nm to 760 nm.

The present invention may be used as a high precision living body light measuring device and a light source using plural wavelengths.

What is claimed is:

1. An optical measurement instrument for a living body, the instrument comprising:
    a light source adapted to emit a plurality of optical signals to the surface of a living body; and
    a light-receiving device that detects the plurality of optical signals emitted from a surface of the living body after the optical signals have passed through an interior of the living body,
    wherein the light source includes a plurality of semiconductor light-emitting devices having mutually different wavelengths from the visible to the infrared mounted on a sub-mount, a driving circuit connected to the plurality of semiconductor light-emitting devices that controls output of the optical signals and emits optical signals of different wavelengths, and one optical output power monitoring device that detects the optical signals emitted from the plurality of semiconductor light-emitting devices, these elements being housed in one package,
    the output of the optical signals by the plurality of semiconductor light-emitting devices is controlled by feeding power output signals corresponding to the plurality of optical signals detected by the optical output power monitoring device back to the driving circuit connected to the semiconductor light-emitting devices that emit the optical signals of different wavelengths,
    a signal separation circuit that receives the power output signals and separates the power output signals for each wavelength of the plurality of optical signals corresponding to the power output signals, and
    the output of the optical signals is controlled to remain constant according to the power output signals separated by the signal separation circuit.

2. The optical measurement instrument for a living body according to claim 1, wherein the optical signals emitted from the plurality of semiconductor light-emitting devices contain two wavelengths selected so that the difference between the absorption coefficient for each wavelength of the optical signals emitted from the plurality of semiconductor light-emitting devices to a plurality of biological materials forming the living body is greater than a predetermined value, and at least one wavelength intermediate between these two wavelengths.

3. The optical measurement instrument for a living body according to claim 1, wherein the shortest wavelength among the wavelengths of the plurality of optical signals is 705±5 nm.

4. The optical measurement instrument for a living body according to claim 1, wherein the plurality of optical signals have wavelengths including 755±5 nm.

5. The optical measurement instrument for a living body according to claim 1, wherein detection of the plurality of optical signals emitted from the surface of the living body after the optical signals have passed through the interior of the living body by the light-receiving device is utilized to detect a blood deoxy-hemoglobin concentration of the living body to which the light source is directed.

6. The optical measurement instrument for a living body according to claim 5, having a device to cause the light emitted from the semiconductor light-emitting devices to diverge.

7. The optical measurement instrument for a living body according to claim 5, wherein the wavelength fluctuation of the semiconductor light-emitting devices in the usage environment is within ±5 nm for each semiconductor light-emitting device.

8. The optical measurement instrument for a living body according to claim 5, wherein the reflectance of a light-emitting facet at the wavelength of the light emitted from the light-emitting facet, is 50% or more.

9. The optical measurement instrument for a living body according to claim 5, wherein the semiconductor light-emitting devices perform self-pulsation.

10. The optical measurement instrument for a living body according to claim 1, wherein at least one of the semiconductor light-emitting devices has an emission layer including an $In_{1-x}Ga_xAs_yP_{1-y}$ quantum well layer having a lattice constant $a_w$ in the surface and a barrier layer provided on a GaAs substrate having a lattice constant a, wherein the emission layer is such that the strain $\epsilon$ defined by $\epsilon(\%)=(a_w-a)/a\times100$ satisfies $0.4\%<\epsilon<1.4\%$, wherein y in the composition satisfies $0.10<y<0.45$, and the wavelength of the emitted light is from 700 nm to 760 nm.

11. The optical measurement instrument for a living body according to claim 1, wherein at least one of the semiconductor light-emitting devices has an emission layer including an $In_{1-x}Ga_xAs_yP_{1-y}$ quantum well layer having a lattice constant $a_w$ in the surface and a barrier layer provided on a GaAs substrate having a lattice constant a, wherein the emission layer is such that the strains $\epsilon$ defined by $\epsilon(\%)=(a_w-a)/a\times100$ satisfies $0.4\%<\epsilon<1.2\%$, wherein y in the composition satisfies $0.10<y<0.25$, and the wavelength of the emitted light is from 700 nm to 730 nm.

12. The optical measurement instrument for a living body according to claim 1, wherein at least one of the semiconductor light-emitting devices has an emission layer including an $In_{1-x}Ga_xAs_yP_{1-y}$ quantum well layer having a lattice constant $a_w$ in the surface and a barrier layer provided on a GaAs substrate having a lattice constant a, wherein: the emission layer is such that the strains $\epsilon$ defined by $\epsilon(\%)=(a_w-a)/a\times100$ satisfies $0.4\%<\epsilon<0.9\%$, wherein y in the composition satisfies $0.10<y<0.20$, and the wavelength of the emitted light is from 700 nm to 720 nm.

13. The optical measurement instrument for a living body according to claim 1, wherein at least one of the semiconductor light-emitting devices has an emission layer including an $In_{1-x}Ga_xAs_yP_{1-y}$ quantum well layer having a lattice constant $a_w$ in the surface and a barrier layer provided on a GaAs substrate having a lattice constant a, wherein the emission layer is such that the strains $\epsilon$ defined by $\epsilon(\%)=(a_w-a)/a\times100$ satisfies $0.6\%<\epsilon<1.4\%$, wherein y in the composition satisfies $0.20<y<0.35$, and the wavelength of the emitted light is from 725 nm to 760 nm.

* * * * *

UNITED STATES PATENT AND TRADEMARK OFFICE
CERTIFICATE OF CORRECTION

| | | |
|---|---|---|
| PATENT NO. | : 8,369,913 B2 | Page 1 of 1 |
| APPLICATION NO. | : 11/984279 | |
| DATED | : February 5, 2013 | |
| INVENTOR(S) | : Nomoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1339 days.

Signed and Sealed this
Eleventh Day of November, 2014

Michelle K. Lee
*Deputy Director of the United States Patent and Trademark Office*